United States Patent [19]
Baichwal

[11] Patent Number: 5,554,387
[45] Date of Patent: Sep. 10, 1996

[54] SUSTAINED RELEASE HETERODISPERSE HYDROGEL SYSTEMS FOR INSOLUBLE DRUGS

[75] Inventor: Anand R. Baichwal, Wappingers Falls, N.Y.

[73] Assignee: Edward Mendell Co., Ltd., Patterson, N.Y.

[21] Appl. No.: 447,236

[22] Filed: May 22, 1995

Related U.S. Application Data

[62] Division of Ser. No. 118,924, Sep. 9, 1993, Pat. No. 5,455,046.

[51] Int. Cl.⁶ ........................................... A61K 9/14
[52] U.S. Cl. .......................... 424/488; 514/964; 524/55
[58] Field of Search ................. 424/488; 524/55; 514/964

[56] References Cited

U.S. PATENT DOCUMENTS

| | | | |
|---|---|---|---|
| 4,412,986 | 11/1983 | Kawata et al. | 424/80 |
| 4,562,069 | 12/1985 | Hegasy et al. | 424/80 |
| 4,673,564 | 6/1987 | Kawata et al. | 424/494 |
| 4,765,990 | 8/1988 | Sugimoto et al. | 424/494 |
| 4,792,452 | 12/1988 | Howard et al. | 424/475 |
| 4,808,413 | 2/1989 | Joshi | 424/458 |
| 4,867,985 | 9/1989 | Heafield et al. | 424/461 |
| 4,892,741 | 1/1990 | Ohm et al. | 424/479 |
| 4,904,699 | 2/1990 | Bauer | 514/972 |
| 4,942,040 | 7/1990 | Ragnarssor et al. | 424/486 |
| 4,973,469 | 11/1990 | Mulligan et al. | 424/461 |
| 4,994,276 | 2/1991 | Baichwal et al. | 424/440 |
| 5,007,790 | 4/1991 | Shell | 424/451 |
| 5,051,263 | 9/1991 | Barry et al. | 424/490 |
| 5,071,642 | 12/1991 | Lahr et al. | 424/474 |
| 5,128,143 | 7/1992 | Baichwal et al. | 424/464 |
| 5,135,757 | 8/1992 | Baichwal et al. | 424/465 |
| 5,145,683 | 9/1992 | Rhodes | 424/451 |
| 5,455,046 | 10/1995 | Baichwal | 424/457 |

FOREIGN PATENT DOCUMENTS

| | | |
|---|---|---|
| 1288049 | 8/1991 | Canada . |
| 0232155 | 8/1987 | European Pat. Off. . |
| 0357793 | 3/1990 | European Pat. Off. . |
| 8902738 | 4/1989 | WIPO . |
| 9206680 | 4/1992 | WIPO . |

*Primary Examiner*—Nathan M. Nutter
*Attorney, Agent, or Firm*—Steinberg, Raskin & Davidson, P.C.

[57] ABSTRACT

A sustained release pharmaceutical formulation includes a sustained release excipient including a gelling agent, an inert pharmaceutical diluent, an optional cationic cross-linking agent, and a medicament having moderate to poor solubility is disclosed. In certain embodiments, the sustained release excipient is granulated with a solution or suspension of a hydrophobic polymer in an amount effective to slow the hydration of the gelling agent when the formulation is exposed to an environmental fluid. In another embodiment, the tablet is coated with a hydrophobic polymer.

18 Claims, No Drawings

SUSTAINED RELEASE HETERODISPERSE HYDROGEL SYSTEMS FOR INSOLUBLE DRUGS

This is a divisional of application Ser. No. 08/118,924 filed Sep. 9, 1993 and now U.S. Pat. No. 5,455,046.

BACKGROUND OF THE INVENTION

The advantages of controlled release products are well known in the pharmaceutical field and include the ability to maintain a desired blood level of a medicament over a comparatively longer period of time while increasing patient compliance by reducing the number of administrations necessary to achieve the same. These advantages have been attained by a wide variety of methods. For example, different hydrogels have been described for use in controlled release medicines, some of which are synthetic, but most of which are semi-synthetic or of natural origin. A few contain both synthetic and non-synthetic material. However, some of the systems require special process and production equipment, and in addition some of these systems are susceptible to variable drug release.

Oral controlled release delivery systems should ideally be adaptable so that release rates and profiles can be matched to physiological and chronotherapeutic requirements.

While many controlled and sustained release formulations are already known, certain moderately to poorly soluble drugs present formulation difficulties which render them inapplicable for sustained release formulations which might be suitable for, e.g., relatively soluble drugs. It is often not possible to readily predict whether a particular sustained release formulation will provide the desired sustained release for a relatively insoluble drug, and it has generally been found that it is necessary to carry out considerable experimentation to obtain sustained release formulations of such drugs having the desired bioavailability when ingested.

An example of a poorly soluble drug is nifedipine, which is very poorly soluble, and often exhibits poor bioavailability when incorporated into sustained release formulations. Accordingly, a great deal of attention has been given to the preparation of sustained release nifedipine formulations which provide acceptable bioavailability. Certain prior art, such as U.S. Pat. No. 4,765,989 (Wong, et al.) describe an osmotic system wherein nifedipine is contained along with osmopolymers in a compartment enclosed by a wall which is substantially impermeable to the passage of the drug. The osmopolymer exhibits an osmotic pressure gradient across the wall against the external fluid. A passageway in the wall communicates with the first composition and the exterior of the device for delivering nifedipine to the passageway.

Other techniques which have been described in the prior art for preparing sustained release nifedipine formulations include the transformation of crystalline nifedipine into fine powder, the transformation of the crystalline nifedipine to the amorphous form, the formation of clathrates or compounds of inclusion with betacyclodextrines, and the formation of solid solutions with polyethylene glycols.

Still other techniques are directed to processes for increasing the bioavailability of nifedipine. U.S. Pat. No. 4,880,623 (Piergiorgio, et al.) describes a process wherein nifedipine and polyethylene glycol are coprecipitated from a solution into a product in the form of very fine particles having an extremely high total specific surface. In one embodiment, substances which swell upon contact with the gastrointestinal juices and successively dissolve slowly (selected from hydroxypropylmethyl cellulose, methyl cellulose, hydroxypropyl cellulose, carboxyvinyl polymers, xanthan gum) in quantities from 5–50% of the tablet are added so as to obtain the prolongation of the retard effect.

Previously, a heterodisperse polysaccharide excipient system and controlled release oral solid dosage forms were described in our U.S. Pat. Nos. 4,994,276, 5,128,143, and 5,135,757. These systems are commercially available under the tradename TIMERx™ from Edward Mendell Co., Inc., Patterson, N.Y., which is the assignee of the present invention. These patents are hereby incorporated by reference.

OBJECTS AND SUMMARY OF THE INVENTION

It is an object of the present invention to provide a sustained release formulation for an insoluble therapeutically active medicament.

It is a further object of the present invention to provide a method for preparing a bioavailable sustained release formulation for an poorly soluble therapeutically active medicament.

It is yet another object of the present invention to provide a sustained release excipient which may be used in the preparation of a sustained release oral solid dosage form of a poorly soluble therapeutically active medicament.

It is a further object of the present invention to provide a sustained release excipient which is suitable for providing, when combined with a medicament, a sustained release formulation which provides therapeutically effective blood levels of the medicament for e.g., 12 or 24 hours.

It is a further object of the present invention to provide a sustained release drug delivery system wherein acceptable bioavailability of an otherwise poorly bioavailable therapeutically active agent is achieved.

The above-mentioned objects and others are achieved by virtue of the present invention, which relates in part to a controlled release formulation comprising a therapeutically effective amount of a medicament having a solubility less than about 10 g/l, and a controlled release excipient comprising a gelling agent, an inert diluent selected from, e.g., a monosaccharide, a disaccharide, a polyhydric alcohol, or mixtures thereof, and an effective amount of a pharmaceutically acceptable water-soluble cationic cross-linking agent.

More particularly, the present invention is related to a sustained release oral solid dosage form comprising an effective amount of medicament having a solubility of less than about 10 g/l to render a therapeutic effect; a sustained release excipient comprising a gelling agent, an inert pharmaceutical diluent, and an effective amount of a pharmaceutically acceptable cationic cross-linking agent to provide a sustained release of the medicament when the dosage form is exposed to an environmental fluid. The ratio of medicament to gelling agent is preferably from about 1:3 to about 1:8. The resulting tablet preferably provides a therapeutically effective blood level of the medicament for at least about 12 hours, and in certain preferred embodiments, for about 24 hours.

In certain additional preferred embodiments, the medicament is poorly soluble, i.e., has a solubility of less than about 1,000 mg/l. In especially preferred embodiments, the medicament is nifedipine.

The present invention is also related to a method for providing a sustained release formulation of a medicament having poor solubility in water, comprising preparing a sustained release excipient comprising from about 10 to about 99% by weight of a gelling agent, from about 1 to about 20% by weight of a cationic cross-linking agent, and from about 0 to about 89% by weight of an inert pharmaceutical diluent; and thereafter adding an effective amount of a medicament having a solubility of less than about 10 g/l to render a desired therapeutic effect, and thereafter tableting the resulting mixture such that a product is obtained having a ratio of medicament to gelling agent from about 1:3 to about 1:8, such that the gel matrix is created when the tablet is exposed to an environmental fluid. The resulting tablet provides therapeutically effective blood levels of the medicament for at least about 12 hours, and preferably about 24 hours.

The present invention is further related to a method of treating a patient by orally administering an oral solid dosage form as set forth above.

In certain preferred embodiments, the mixture of the gelling agent, inert diluent, and cationic cross-linking agent are granulated with a dispersion or solution of a hydrophobic material in an amount sufficient to slow the hydration of the gelling agent without disrupting the same.

The present invention is further related to a sustained release oral solid dosage form for absorption of a therapeutically active medicament in the gastrointestinal tract, comprising an effective amount of a medicament having a solubility of less than about 10 g/l to render a therapeutic effect; and a sustained release excipient comprising a gelling agent comprising a heteropolysaccharide gum and a homopolysaccharide gum capable of cross-linking said heteropolysaccharide gum when exposed to an environmental fluid and an inert pharmaceutical diluent, the sustained release excipient being granulated with a solution or a dispersion of a hydrophobic material in an amount effective to slow the hydration of the gelling agent without disrupting the hydrophilic matrix.

In a particularly preferred embodiment, the medicament comprises a therapeutically effective dihydropyridine such as nifedipine.

By "sustained release" it is meant for purposes of the present invention that the therapeutically active medicament is released from the formulation at a controlled rate such that therapeutically beneficial blood levels (but below toxic levels) of the medicament are maintained over an extended period of time, e.g., providing a 12 hour or a 24 hour dosage form.

By "bioavailable" it is meant for purposes of the present invention that the therapeutically active medicament is absorbed from the sustained release formulation and becomes available in the body at the intended site of drug action.

By "poorly soluble", it is meant that the therapeutically active medicament has an aqueous solubility of less than about 1000 milligrams per liter (mg/l).

By "moderately soluble", it is meant that the therapeutically active medicament has an aqueous solubility of less than about 10 grams per liter (g/l).

The term "environmental fluid" is meant for purposes of the present invention to encompass, e.g. , an aqueous solution, or gastrointestinal fluid.

DETAILED DESCRIPTION

As reported in our previously in our U.S. Pat. Nos. 4,994,276, 5,128,143, and 5,135,757, the heterodisperse excipient of the present invention comprises a gelling agent of both hetero- and homo- polysaccharides which exhibit synergism, e.g., the combination of two or more polysaccharide gums produce a higher viscosity and faster hydration than that which would be expected by either of the gums alone, the resultant gel being faster-forming and more rigid.

In the present invention, it has been found that a sustained release excipient comprising only the gelling agent (heterodisperse polysaccharide, e.g., xanthan gum and locust bean gum) may not be sufficient to provide a suitable sustained release of an insoluble medicament to provide a 24 hour formulation, nor to prevent an initial "burst" of drug release from the formulation when the formulation is exposed to a fluid in an environment of use, e.g. an aqueous solution or gastrointestinal fluid. This is especially the case with certain medicaments such as those which are only moderately soluble, and is especially true with drugs such as nifedipine which are only poorly soluble.

This problem has been overcome by virtue of the present invention, which is related in part to the surprising discovery that by including a cationic crosslinking agent in the sustained release excipient, the gel strength of the formulation is significantly increased.

In certain embodiments, the present invention is related to the surprising discovery that by granulating the sustained release excipient with a solution or dispersion of a hydrophobic polymer prior to admixture of the sustained release excipient with the medicament and tableting, the medicament may provide therapeutically effective blood levels for extended periods of time, e.g., from about 12 to about 24 hours.

In certain preferred embodiments of the present invention, the sustained release excipient is prepared by mixing the gelling agent, the cationic crosslinking agent, and the inert diluent. Thereafter, the mixture is granulated with a solution or dispersion of a hydrophobic polymer in an amount effective to slow the hydration of the gelling agent without disrupting the hydrophilic matrix. Next, the insoluble medicament is added, and the resultant mixture is tableted.

In other preferred embodiments of the present invention, the tablets prepared as set forth above are then coated with a hydrophobic polymer to a weight gain from about 1 to about 20 percent by weight.

The term "heteropolysaccharide" as used in the present invention is defined as a water-soluble polysaccharide containing two or more kinds of sugar units, the heteropolysaccharide having a branched or helical configuration, and having excellent water-wicking properties and immense thickening properties.

An especially preferred heteropolysaccharide is xanthan gum, which is a high molecular weight ($>10^6$) heteropolysaccharide. Other preferred heteropolysaccharides include derivatives of xanthan gum, such as deacylated xanthan gum, the carboxymethyl ether, and the propylene glycol ester.

The homopolysaccharide gums used in the present invention which are capable of cross-linking with the heteropolysaccharide include the galactomannans, i.e., polysaccharides which are composed solely of mannose and galactose. Galactomannans which have higher proportions of unsubstituted mannose regions have been found to achieve more interaction with the heteropolysaccharide. Locust bean gum, which has a higher ratio of mannose to the galactose, is especially preferred as compared to other galactomannans such as guar and hydroxypropyl guar.

The controlled release properties of the controlled release formulations of the present invention may be optimized when the ratio of heteropolysaccharide gum to homopolysaccharide material is about 1:1, although heteropolysaccharide gum in an amount of from about 20 to about 80 percent or more by weight of the heterodisperse polysaccharide material provides an acceptable slow release product. The combination of any homopolysaccharide gums known to produce a synergistic effect when exposed to aqueous solutions may be used in accordance with the present invention. It is also possible that the type of synergism which is present with regard to the gum combination of the present invention could also occur between two homogeneous or two heteropolysaccharides. Other acceptable gelling agents which may be used in the present invention include those gelling agents well-known in the art. Examples include vegetable gums such as alginates, carrageenan, pectin, guar gum, xanthan gum, modified starch, hydroxypropylmethylcellulose, methylcellulose, and other cellulosic materials such as sodium carboxymethylcellulose and hydroxypropyl cellulose. This list is not meant to be exclusive.

The combination of xanthan gum with locust bean gum with or without the other homopolysaccharide gums is an especially preferred gelling agent. The chemistry of certain of the ingredients comprising the excipients of the present invention such as xanthan gum is such that the excipients are considered to be self-buffering agents which are substantially insensitive to the solubility of the medicament and likewise insensitive to the pH changes along the length of the gastrointestinal tract.

The inert filler of the sustained release excipient preferably comprises a pharmaceutically acceptable saccharide, including a monosaccharide, a disaccharide, or a polyhydric alcohol, and/or mixtures of any of the foregoing. Examples of suitable inert pharmaceutical fillers include sucrose, dextrose, lactose, microcrystalline cellulose, fructose, xylitol, sorbitol, mixtures thereof and the like. However, it is preferred that a soluble pharmaceutical filler such as lactose, dextrose, sucrose, or mixtures thereof be used.

The cationic cross-linking agent which is optionally used in conjunction with the present invention may be monovalent or multivalent metal cations. The preferred salts are the inorganic salts, including various alkali metal and/or alkaline earth metal sulfates, chlorides, borates, bromides, citrates, acetates, lactates, etc. Specific examples of suitable cationic cross-linking agents include calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate and sodium fluoride. Multivalent metal cations may also be utilized. However, the preferred cationic cross-linking agents are bivalent. Particularly preferred salts are calcium sulfate and sodium chloride. The cationic cross-linking agents of the present invention are added in an amount effective to obtain a desirable increased gel strength due to the cross-linking of the gelling agent (e.g., the heteropolysaccharide and homopolysaccharide gums). In preferred embodiments, the cationic cross-linking agent is included in the sustained release excipient of the present invention in an amount from about 1 to about 20% by weight of the sustained release excipient, and in an amount 0.5% to about 16% by weight of the final dosage form.

In certain embodiments of the present invention, the sustained release excipient comprises from about 10 to about 99 percent by weight of a gelling agent comprising a heteropolysaccharide gum and a homopolysaccharide gum, from about 1 to about 20 percent by weight of a cationic crosslinking agent, and from about 0 to about 89 percent by weight of an inert pharmaceutical diluent. In other embodiments, the sustained release excipient comprises from about 10 to about 75 percent gelling agent, from about 2 to about 15 percent cationic crosslinking agent, and from about 30 to about 75 percent inert diluent. In yet other embodiments, the sustained release excipient comprises from about 30 to about 75 percent gelling agent, from about 5 to about 10 percent cationic cross-linking agent, and from about 15 to about 65 percent inert diluent.

The sustained release excipient of the present invention (with or without the optional cationic cross-linking agent) may be further modified by incorporation of a hydrophobic material which slows the hydration of the gums without disrupting the hydrophilic matrix. This is accomplished in preferred embodiments of the present invention by granulating the sustained release excipient with the solution or dispersion of a hydrophobic material prior to the incorporation of the medicament. The hydrophobic polymer may be selected from an alkylcellulose such as ethylcellulose, other hydrophobic cellulosic materials, polymers or copolymers derived from acrylic or methacrylic acid esters, copolymers of acrylic and methacrylic acid esters, zein, waxes, shellac, hydrogenated vegetable oils, and any other pharmaceutically acceptable hydrophobic material known to those skilled in the art. The amount of hydrophobic material incorporated into the sustained release excipient is that which is effective to slow the hydration of the gums without disrupting the hydrophilic matrix formed upon exposure to an environmental fluid. In certain preferred embodiments of the present invention, the hydrophobic material is included in the sustained release excipient in an amount from about 1 to about 20 percent by weight. The solvent for the hydrophobic material may be an aqueous or organic solvent, or mixtures thereof.

Examples of commercially available alkylcelluloses are Aquacoat® (aqueous dispersion of ethylcellulose available from FMC) and Surelease® (aqueous dispersion of ethylcellulose available from Colorcon). Examples of commercially available acrylic polymers suitable for use as the hydrophobic material include Eudragit® RS and RL (copolymers of acrylic and methacrylic acid esters having a low content (e.g, 1:20 or 1:40) of quaternary ammonium compounds).

Once the sustained release excipient of the present invention has been prepared, it is then possible to blend the same with the medicament, e.g., in a high shear mixer. The medicaments which are useful in the present invention preferably have moderate ($\geq 10$ g/l) to poor ($\geq 1,000$ mg/l) solubility. In certain especially preferred embodiments, the medicament is a therapeutically effective dihydropyridine. Dihydropyridines such as nifedipine have an aqueous solubility of less than about 1,000 mg/l. Dihydropyridines are useful for the treatment of circulatory disorders and high blood pressure. Useful formulations of dihydropyridines generally contain doses from about 10 mg to about 240 mg. The production of dihydropyridines is well known in the art, and is described, for example, in British Patent 11 73 862. An especially preferred dihydropyridine is nifedipine. Other suitable dihydropyridines include nimodipine, nivaldipine, nitrendipine, nisolidipine, niludipine, nicardipine and felodipine. This list is not meant to be exclusive, and many other dihydropyridines and indeed other medicaments having similar solubility and/or bioavailability problems may also be used successfully in conjunction with the present invention. In certain preferred embodiments of the present invention, the dosage form includes a dosage of nifedipine in an amount of 20 mg, 30 mg, 60 mg, or 90 mg.

It has been found that it is important to include an effective amount of a wetting agent in the formulation in order to increase the bioavailability of drugs with poor solubility, such as nifedipine. The wetting agent may be added, e.g., by spraying while mixing the granulate.

Suitable wetting agents for use in conjunction with the present invention include polyethyleneglycols as esters or ethers. Examples include polyethoxylated castor oil, polyethoxylated hydrogenated castor oil, polyethoxylated fatty acid from castor oil or polyethoxylated fatty acid from castor oil or polyethoxylated fatty acid from hydrogenated castor oil. Commercially available wetting agents which can be used are known under trade names Cremophor, Myrj, Polyoxyl 40 stearate, Emerest 2675, Lipal 395 and PEG 3350. An especially preferred wetting agent is polyethyleneglycol having a molecular weight of 3,350 (i.e., PEG 3350).

The wetting agent is dissolved in a suitable solvent such as water, and is thereafter added to the blended mixture of the sustained release excipient and the medicament. This allows the wetting agent to wet the particles of the excipient such that when the solvent evaporates the particles of the medicament which precipitate are tiny and do not aggregate. A granulate of the medicament and the wetting agent is obtained which is preferably finely and homogenously dispersed in the excipient.

The wetting agent is preferably included in an amount effective to provide a final sustained release product having acceptable bioavailability. For example, in certain embodiments of the present invention wherein the medicament is nifedipine, the wetting agent is included in an amount from about 5% to about 10% of the final product, by weight.

In certain embodiments of the embodiment a hydrophobic polymer is added to the mixture of wetting agent and medicament. The hydrophobic polymer may be, e.g., an alkylcellulose such as ethylcellulose, other hydrophobic cellulosic materials, polymers or copolymers derived from acrylic or methacrylic acid esters, zein, waxes, other hydrophobic cellulosic materials, hydrogenated vegetable oils, and any other pharmaceutically acceptable hydrophobic material known to those skilled in the art.

The hydrophobic material may be dissolved in an organic solvent or dispersed in an aqueous solution. Thereafter, the hydrophobic material may be used to coat the granulate of medicament/wetting agent/sustained release excipient. The granulate may be coated with the hydrophobic coating to a weight gain of, e.g., from about 1 to about 20 percent, and preferably from about 5 to about 10 percent. The granulation is then preferably dried. Thereafter, the granulate may be further formulated into an appropriate oral dosage form, for example, by compression of the resulting granulate into appropriately sized tablets, by filling gelatin capsules with an appropriate amount of the granulate (with or without compression of the granulate), as well as use in the manufacture of other oral dosage forms known to those skilled in the art. This embodiment may be particularly beneficial to reduce the amount of drug released during the initial phases of dissolution when the formulation is exposed to fluid in an environment of use, e.g., in-vitro dissolution or in the gastrointestinal tract.

An effective amount of any generally accepted pharmaceutical lubricant, including the calcium or magnesium soaps may be added to the above-mentioned ingredients of the excipient be added at the time the medicament is added, or in any event prior to compression into a said dosage form.

An example of a suitable lubricant is magnesium stearate in an amount of about 0.5 to about 3% by weight of the solid dosage form. An especially preferred lubricant is sodium stearyl fumarate, NF, commercially available under the trade name Pruv® from the Edward Mendell Co., Inc.

The sustained release excipients of the present invention have uniform packing characteristics over a range of different particle size distributions and are capable of processing into the final dosage form (e.g., tablets) using either direct compression, following addition of drug and lubricant powder, or conventional wet granulation.

The properties and characteristics of a specific excipient system prepared according to the present invention is dependent in part on the individual characteristics of the homo and heteropolysaccharide constituents, in terms of polymer solubility, glass transition temperatures etc., as well as on the synergism both between different homo- and heteropolysaccharides and between the homo and heteropolysaccharides and the inert saccharide constituent(s) in modifying dissolution fluid-excipient interactions.

The combination of the gelling agent (i.e., a mixture of xanthan gum and locust bean gum) with the inert diluent, with or without the cationic cross-linking agent and hydrophobic polymer, provides a ready-to-use product in which a formulator need only blend the desired active medicament and an optional lubricant with the excipient and then compress the mixture to form slow release tablets. The excipient may comprise a physical admix of the gums along with a soluble excipient such as compressible sucrose, lactose or dextrose, although it is preferred to granulate or agglomerate the gums with plain (i.e., crystalline) sucrose, lactose, dextrose, etc., to form an excipient. The granulate form has certain advantages including the fact that it can be optimized for flow and compressibility; it can be tableted, formulated in a capsule, extruded and spheronized with an active medicament to form pellets, etc.

The pharmaceutical excipients prepared in accordance with the present invention may be prepared according to any agglomeration technique to yield an acceptable excipient product. In wet granulation techniques, the desired amounts of the heteropolysaccharide gum, the homopolysaccharide gum, and the inert diluent are mixed together and thereafter a moistening agent such as water, propylene glycol, glycerol, alcohol or the like is added to prepare a moistened mass. Next, the moistened mass is dried. The dried mass is then milled with conventional equipment into granules. Therefore, the excipient product is ready to use.

The sustained release excipient is free-flowing and directly compressible. Accordingly, the excipient may be mixed in the desired proportion with a therapeutically active medicament and optional lubricant (dry granulation). Alternatively, all or part of the excipient may be subjected to a wet granulation with the active ingredient and thereafter tableted. When the final product to be manufactured is tablets, the complete mixture, in an amount sufficient to make a uniform batch of tablets, is then subjected to tableting in a conventional production scale tableting machine at normal compression pressure, i.e. about 2000–1600 lbs/sq in. However, the mixture should not be compressed to such a degree that there is subsequent difficulty in its hydration when exposed to gastric fluid.

One of the limitations of direct compression as a method of tablet manufacture is the size of the tablet. If the amount of active is high a pharmaceutical formulator may choose to wet granulate the active with other excipients to attain a decent size tablet with the right compact strength. Usually the amount of filler/binder or excipients needed in wet granulation is less than that in direct compression since the process of wet granulation contributes to some extent toward the desired physical properties of a tablet.

The average tablet size for round tablets is preferably about 300 mg to 750 mg and for capsule-shaped tablets about 750 mg to 1000 mg.

The average particle size of the granulated excipient of the present invention ranges from about 50 microns to about 400 microns and preferably from about 185 microns to about 265 microns. The particle size of the granulation is not narrowly critical, the important parameter being that the average particle size of the granules, must permit the formation of a directly compressible excipient which forms pharmaceutically acceptable tablets. The desired tap and bulk densities of the granulation of the present invention are normally between from about 0.3 to about 0.8 g/ml, with an average density of from about 0.5 to about 0.7 g/ml. For best results, the tablets formed from the granulations of the present invention are from about 6 to about 8 kg hardness. The average flow of the granulations prepared in accordance with the present invention are from about 25 to about 40 g/sec. Tablets compacted using an instrumented rotary tablet machine have been found to possess strength profiles which are largely independent of the inert saccharide component. Scanning electron photomicrographs of largely tablet surfaces have provided qualitative evidence of extensive plastic deformation on compaction, both at the tablet surface and across the fracture surface, and also show evidence of surface pores through which initial solvent ingress and solution egress may occur.

In certain embodiments of the invention, the tablet is coated with a sufficient amount of a hydrophobic polymer to render the formulation capable of providing a release of the medicament such that a 12 or 24 hour formulation is obtained. The hydrophobic polymer which included in the tablet coating may be the same or different material as compared to the hydrophobic polymeric material which is optionally granulated with the sustained release excipient.

In other embodiments of the present invention, the tablet coating may comprise an enteric coating material in addition to or instead or the hydrophobic polymer coating. Examples of suitable enteric polymers include cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures of any of the foregoing. An example of a suitable commercially available enteric material is available under the trade name Eudragit™ L 100-555.

In further embodiments, the dosage form may be coating with a hydrophilic coating in addition to or instead of the above-mentioned coatings. An example of a suitable material which may be used for such a hydrophilic coating is hydroxypropylmethylcellulose (e.g., Opadry®, commercially available from Colorcon, West Point, Pa.).

The coatings may be applied in any pharmaceutically acceptable manner known to those skilled in the art. For example, in one embodiment, the coating is applied via a fluidized bed or in a coating pan. For example, the coated tablets may be dried, e.g., at about 60°–70° C. for about 3–4 hours in a coating pan. The solvent for the hydrophobic polymer or enteric coating may be organic, aqueous, or a mixture of an organic and an aqueous solvent. The organic solvents may be, e.g., isopropyl alcohol, ethanol, and the like, with or without water.

In additional embodiments of the present invention, a support platform is applied to the tablets manufactured in accordance with the present invention. Suitable support platforms are well known to those skilled in the art. An example of suitable support platforms is set forth, e.g., in U.S. Pat. No. 4,839,177, hereby incorporated by reference. In that patent, the support platform partially coats the tablet, and consists of a polymeric material insoluble in aqueous liquids. The support platform may, for example, be designed to maintain its impermeability characteristics during the transfer of the therapeutically active medicament. The support platform may be applied to the tablets, e.g., via compression coating onto part of the tablet surface, by spray coating the polymeric materials comprising the support platform onto all or part of the tablet surface, or by immersing the tablets in a solution of the polymeric materials.

The support platform may have a thickness of, e.g., about 2 mm if applied by compression, and about 10μ if applied via spray-coating or immersion-coating. Generally, in embodiments of the invention wherein a hydrophobic polymer or enteric coating is applied to the tablets, the tablets are coated to a weight gain from about 1 to about 20%, and in certain embodiments preferably from about 5% to about 10%.

Materials useful in the hydrophobic coatings and support platforms of the present invention include derivatives of acrylic acid (such as esters of acrylic acid, methacrylic acid, and copolymers thereof) celluloses and derivatives thereof (such as ethylcellulose), polyvinylalcohols, and the like.

In certain embodiments of the present invention, the tablet core includes an additional dose of the medicament included in either the hydrophobic or enteric coating, or in an additional overcoating coated on the outer surface of the tablet core (without the hydrophobic or enteric coating) or as a second coating layer coated on the surface of the base coating comprising the hydrophobic or enteric coating material. This may be desired when, for example, a loading dose of a therapeutically active agent is needed to provide therapeutically effective blood levels of the active agent when the formulation is first exposed to gastric fluid. The loading dose of medicament included in the coating layer may be, e.g., from about 10% to about 40% of the total amount of medicament included in the formulation.

DETAILED DESCRIPTION OF THE PREFERRED EMBODIMENTS

The following examples illustrate various aspects of the present invention. They are not to be construed to limit the claims in any manner whatsoever.

EXAMPLES 1–3

Effect of Calcium Sulfate in Excipient

In Examples 1–3, sustained release excipients in accordance with the present invention are first prepared, the medicament (in this case nifedipine) being added subsequently, and the final mixture then being tableted.

The sustained release excipient is prepared by dry blending the requisite amounts of xanthan gum, locust bean gum, calcium sulfate, and dextrose in a high speed mixer/granulator for 3 minutes. While running choppers/impellers, water (125–150 ml) is added to the dry blended mixture, and granulated for another 3 minutes. The granulation is then dried in a fluid bed dryer to a LOD (loss on drying) of less than about 10% by weight (e.g., 4–7% LOD). The granulation is then milled using 20 mesh screens. The ingredients of the granulations of Examples 1–3 are set forth in Table 1 below:

TABLE 1

PREPARATION OF SUSTAINED-RELEASE EXCIPIENT

| Component | % - Ex. 1 | % - Ex. 2 | % - Ex.3 |
|---|---|---|---|
| 1. Xanthan Gum | 25 | 25 | 25 |
| 2. Locust Bean Gum | 25 | 25 | 25 |
| 3. Calcium Sulfate | 0 | 5 | 20 |
| 4. Dextrose | 50 | 45 | 30 |
| 5. Water | 150 ml | 123 ml | 123 ml |

Next, the sustained release excipient prepared as detailed above is dry blended with the desired amount of nifedipine along with a suitable amount of wetting agent (PEG 3350) in a V-blender for 15 minutes. A suitable tableting lubricant (Pruv®, sodium stearyl fumarate, NF, commercially available from the Edward Mendell Co., Inc.) is added, and the mixture is blended for another 5 minutes. This final mixture is tableted to approximately 361 mg. The ingredients of the tablets of Examples 1–3 are set forth in Table 2 below:

TABLE 2

TABLET FORMULATION - EXAMPLES 1-3

| Component | % |
|---|---|
| 1. Sustained-Release Excipient | 83.1 |
| 2. Nifedipine | 8.31 |
| 3. PEG 3350 | 8.31 |
| 4. Pruv ® * | 0.25 |

*Sodium Stearyl Fumarate

Dissolution tests were then carried out on the tablets of Examples 1–3. The dissolution tests are conducted in 30% polyethyleneglycol (PEG) 400 and distilled water in an automated USP dissolution apparatus (Paddle type II, 150 rpm), and the amount of drug released was analyzed via UV analysis. The results are set forth in Table 3 below.

TABLE 3

| Time (hr) | Ex. 1 | Ex. 2 | Ex. 3 |
|---|---|---|---|
| 4 | 14.7 | 27.4 | 15.6 |
| 8 | 42.2 | 47.9 | 43.0 |
| 12 | 59.2 | 60.3 | 58.8 |
| 16 | 80.7 | 68.2 | 65.6 |
| 20 | 91.8 | 84.2 | 74.5 |
| 24 | 97.2 | 89.6 | 79.7 |

From the results provided in Table 3, it is evident that the tablets of Examples 1–3 provided suitable 24 hour oral solid dosage forms for nifedipine.

EXAMPLES 4–6

Effect of Compression Force

In Examples 4–6, a sustained release excipient is prepared by dry blending the requisite amounts of xanthan gum, locust bean gum, calcium sulfate, and dextrose in a high speed mixer/granulator for 3 minutes. A slurry of hydrophobic polymer (ethylcellulose) is prepared by dissolving ethyl cellulose in ethyl alcohol. While running choppers/impellers, the slurry is added to the dry blended mixture, and granulated for another 3 minutes. The granulation is then dried in a fluid bed dryer to a LOD (loss on drying) of less than about 10% by weight (e.g., 4–7% LOD). The granulation is then milled using 20 mesh screens. The ingredients of the sustained release excipient of Examples 4–6 are set forth in Table 4 below:

TABLE 4

| Component | % |
|---|---|
| 1. Xanthan Gum | 25 |
| 2. Locust Bean Gum | 25 |
| 3. Calcium Sulfate | 10 |
| 4. Dextrose | 35 |
| 5. Ethyl Cellulose | 5 |
| 6. Ethyl Alcohol | 10* |

*removed during processing

Thereafter, nifedipine tablets are prepared as follows. A suitable amount of PEG 3350 is mixed with water until dissolved. The desired amount of nifedipine is blended with the sustained release excipient as set forth above in a high shear mixer for 3 minutes, and then the PEG 3350 in water solution is added by spraying while mixing for an additional 2 minutes. Next, a desired amount of Surelease® (aqueous dispersion of ethylcellulose commercially available from Colorcon, Inc., West Point, Pa., USA) is added to the mixture by spraying while mixing for an additional 3 minutes. The granulation is dried in a fluid bed dryer to an LOD of less than 10%. The dried granulation is milled using 20 mesh screens. The dried granulation obtained is tableted to approximately 380 mg using different compression forces. In Example 4, the compression force is 2.5 Kp. In Example 5, the compression force is 12.5 Kp. In Example 6, the compression force is 20.0 Kp. The ingredients (percentage) of the tablets of Examples 4–6 are set forth in Table 5 below:

TABLE 5

| Component | % |
|---|---|
| 1. Sustained Release Excipient | 78.9 |
| 2. Nifedipine | 7.9 |
| 3. PEG 3350 | 7.9 |
| 4. Surelease ® | 5.3 |
| 5. Water | 16.8* |

*removed during processing

Tablets prepared in accordance with Examples 4–6 are then tested with regard to dissolution (U.S.P. Apparatus III in 30% PEG 400 at 30 cycles/minutes) and the drug released analyzed via a UV analysis procedure as set forth in Examples 1–3. The dissolution results for the tablets of Examples 4–6 are provided in Table 6 below.

TABLE 6

| Time (hr) | Ex. 4 | Ex. 5 | Ex. 6 |
|---|---|---|---|
| 4 | 34.1 | 33.6 | 37.0 |
| 8 | 69.1 | 66.0 | 71.7 |
| 12 | 87.0 | 86.3 | 88.9 |
| 16 | 94.3 | 93.6 | 95.7 |
| 20 | 97.5 | 97.1 | 98.6 |
| 24 | 98.8 | 98.7 | 100.1 |

As is readily apparent from the results provided in Table 6, there was substantially no difference in the release of medicament from the tablets when manufactured using different compression forces.

EXAMPLES 7-9

Effect of Drug:Gum Ratio

In Examples 7-9, a sustained release excipient is prepared in accordance with the procedures set forth for Examples 4-6. The ingredients of the sustained release excipient of Examples 7-9 are set forth in Table 7 below:

TABLE 7

| Component | % |
|---|---|
| 1. Xanthan Gum | 25 |
| 2. Locust Bean Gum | 25 |
| 3. Calcium Sulfate | 10 |
| 4. Dextrose | 35 |
| 5. Ethyl Cellulose | 5 |
| 6. Ethyl Alcohol | 10* |

*removed during processing

Thereafter, nifedipine tablets are prepared as follows. The sustained release excipient and a suitable amount of nifedipine are blended in a high shear mixer for 3 minutes. PEG 3350 is mixed with Pruv® until dissolved, and the resulting solution is thereafter added to the blend of sustained release excipient and nifedipine by spraying while mixing for an additional 2 minutes. Thereafter, a dispersion of ethylcellulose in ethanol by spraying while mixing for an additional 3 minutes. Then, the granulation is dried in a fluid bed dryer to an LOD of less than 10%. The dried granulation is milled using 20 mesh screens, and tableted to an appropriate weight (about 383 mg, 443 mg and 503 mg for examples 7-9 respectively). The ingredients of the tablets of Examples 7-9 are set forth in Table 8 below:

TABLE 8

| Component | % - Ex. 7 | % - Ex. 8 | % - Ex. 9 |
|---|---|---|---|
| 1. TIMERx® | 78.4 | 81.3 | 83.5 |
| 2. Nifedipine | 7.8 | 6.8 | 6.0 |
| 3. PEG 3350 | 7.8 | 6.8 | 6.0 |
| 4. Ethylcellulose | 5.2 | 4.5 | 4.0 |
| 5. Pruv® | 0.8 | 0.7 | 0.6 |

In Example 7, the drug:gum ratio is about 1:5. In Example 8, the drug:gum ratio is about 1:6. In Example 9, the drug:gum ratio is about 1:8. By "gum" it is meant the combined weight of xanthan gum and locust bean gum.

Tablets prepared in accordance with Examples 7-9 are then tested with regard to dissolution according to the procedure set forth with respect to Examples 4-6. The dissolution results for the Examples 7-9 are provided in Table 9 below.

TABLE 9

| Time (hr) | Ex. 7 | Ex. 8 | Ex. 9 |
|---|---|---|---|
| 4 | 11.3 | 9.0 | 9.3 |
| 8 | 26.9 | 22.1 | 20.4 |
| 12 | 48.8 | 36.5 | 30.8 |
| 16 | 69.5 | 51.2 | 45.0 |
| 20 | 76.3 | 65.2 | 60.4 |
| 24 | 80.8 | 79.9 | 73.0 |

As can be seen from the results provided in Table 9, the rate of release of nifedipine was slower as the amount of gum relative to the amount of drug increased.

EXAMPLES 10-14

Effect of Gum Content

In Examples 10-14, a sustained release excipient is prepared in accordance with the procedures set forth for Examples 4-6. The ingredients of the sustained release excipient of Examples 10-14 are set forth in Table 10 below:

TABLE 10

| | Percent Included | | | | |
|---|---|---|---|---|---|
| Component | Ex. 10 | Ex. 11 | Ex. 12 | Ex. 13 | Ex. 14 |
| Xanthan Gum | 0 | 5 | 12.5 | 25 | 37.5 |
| Locust Bean Gum | 0 | 5 | 12.5 | 25 | 37.5 |
| Calcium Sulfate | 10 | 10 | 10 | 10 | 10 |
| Dextrose | 85 | 75 | 60 | 35 | 10 |
| Ethyl Cellulose | 5 | 5 | 5 | 5 | 5 |
| Ethyl Alcohol | 10* | 10* | 10* | 10* | 10* |

*removed during processing

Thereafter, nifedipine tablets are prepared in accordance with the procedures set forth with respect to Examples 7-9. The dried granulation is tableted to an appropriate weight, approximately 383 mg. The final product has the following ingredients set forth in Table 11 below:

TABLE 11

| Component | % |
|---|---|
| 1. Sustained-Release Excipient | 78.4 |
| 2. Nifedipine | 7.8 |
| 3. PEG 3350 | 7.8 |
| 4. Ethylcellulose | 5.2 |
| 5. Pruv® | 0.8 |

Tablets prepared in accordance with Examples 10-14 are then tested with regard to dissolution according to the procedure set forth with respect to Examples 4-6. The dissolution results for the Examples 10-14 are provided in Tables 12 and 13 below.

TABLE 12

| | Dissolution | | | | |
|---|---|---|---|---|---|
| Time (hr) | Ex. 10 | Ex. 11 | Ex. 12 | Ex. 13 | Ex. 14 |
| 4 | 91.7 | 49.3 | 34.1 | 21.8 | 24.0 |
| 8 | 91.7 | 85.8 | 69.1 | 59.4 | 49.9 |
| 12 | 91.7 | 91.1 | 87.0 | 84.8 | 83.8 |
| 16 | 91.7 | 93.1 | 94.3 | 101.3 | 91.2 |
| 20 | 91.7 | 93.1 | 97.5 | 105.3 | 92.9 |
| 24 | 91.7 | 93.1 | 98.8 | 106.5 | 92.9 |

TABLE 13

| | Dissolution Rate | | | | |
|---|---|---|---|---|---|
| Time (hr) | Ex. 10 | Ex. 11 | Ex. 12 | Ex. 13 | Ex. 14 |
| 4 | 91.7 | 49.3 | 34.1 | 21.8 | 24.0 |
| 8 | 0.0 | 36.5 | 35.0 | 37.6 | 25.9 |
| 12 | 0.0 | 5.3 | 17.9 | 25.4 | 33.9 |
| 16 | 0.0 | 2.0 | 7.3 | 16.5 | 7.4 |
| 20 | 0.0 | 0.0 | 3.2 | 4.0 | 1.7 |
| 24 | 0.0 | 0.0 | 1.3 | 1.2 | 0.0 |

As can be seen from the results provided in Tables 12 and 13, substantially all of the nifedipine was released from the tablets of Example 10 (no gum) and Example 11 (10% gum) in about 4 hours and about 12 hours respectively. Therefore, the tablets of Example 11 might represent a suitable 12 hour preparation. The tablets of Examples 12–14, in contrast, provided a dissolution profile which released the nifedipine over a significantly longer period of time compared to the tablets of Example 11. The tablets of Example 14 (75% gum) did not appear to release 100% of the nifedipine at the end of 24 hours.

EXAMPLE 15

Effect of Coating with Hydrophobic Polymer

In Example 15, a sustained release excipient is prepared in accordance with the procedures set forth for Examples 4–6. The ingredients of the sustained release excipient of Example 15 are set forth in Table 14 below:

TABLE 14

| Component | % |
|---|---|
| 1. Xanthan Gum | 25 |
| 2. Locust Bean Gum | 25 |
| 3. Compactrol | 10 |
| 4. Emdex | 35 |
| 5. Ethyl Cellulose | 5 |
| 6. Ethyl Alcohol | 5* |

*removed during processing

Thereafter, nifedipine tablets are prepared in accordance with the procedures set forth with respect to Examples 4–6. The dried granulation is tableted to approximately 380 mg (target weight is 382.5 mg). The ingredients for the tablets of Example 15 are set forth in Table 15 below.

TABLE 15

| Component | % |
|---|---|
| 1. Sustained-Release Excipient | 78.44 |
| 2. Nifedipine | 7.84 |
| 3. PEG 3350 | 7.84 |
| 4. Pruv ® | 0.24 |
| 5. Surelease ® | 5.64 |
| 6. Ethyl Alcohol | (75 ml)* |

*removed during processing

Thereafter, a portion of the tablets are coated with a hydrophobic polymer. To accomplish this, ethylcellulose (Surelease®, 400 g) is mixed with water (100 g) to form an aqueous suspension. Thereafter, the tablets are coated in a Keith Machinery coating pan (diameter 350 mm; pan speed 20 rpm; spray-gun nozzle 0.8 mm; tablets bed temperature 40°–50° C.; charge per batch 1 kg; dry air—Conair Prostyle 1250, 60°–70° C.). The tablets are coated to a weight gain of about 5%.

Tablets prepared in accordance with Example 15 are then tested with regard to dissolution according to the procedure utilizing USP Method III (USP XXII) at 30 rpm, in 100 ml of distilled water, and the amount of drug released is assayed using an HPLC procedure as set forth below.

The assay method for the nifedipine tablets is as follows:

Mobile phase—Prepare a suitable mixture of water, acetonitrile, and methanol (40:30:30), and degas. Make adjustments if necessary. (Rf. USP XXII, P. 946)

Standard preparation—Dissolve an accurately weighted quantity of USP Nifedipine RS in the methanol (about 1 mg/ml), and dilute with mobile phase to obtain a solution having a known concentration of about 0.1 mg, per ml.

Assay preparation—Weigh and finely powder not less than 20 tablets. Transfer an accurately weighed portion of the powder, equivalent to about 25 mg of Nifedipine to a 250 ml.-volumetric flask. Add about half volume of mobile phase, shake for 15 minutes and sonicate for 15 minutes. Filter through medium-porosity filter paper, wash the remainder with mobile phase up to the volume mark. Mix the solution before use.

Chromatographic system—The liquid chromatograph is equipped with a 265 nm detector and a 25-cm×4.6-mm column that contains 5-μm packing L1. The flow rate is about 1.0-ml per minute. (Cf. Chromatograph the standard preparation, and record the peak responses as directed under procedure. The column efficiency is not less than 16,000 theoretical plates per meter, the tailing factor is not less than 1.5, and the relative standard deviation of the response of the main peak is not more than 1.0%.

Procedure—Separately inject equal volumes (about 25 μL) of the standard preparation and the assay preparation into the chromatograph, record the chromatograms, and measure the response for the major peak. Calculate the quantity, in mg, of C H N O in the portion of nifedipine taken by the formula:

$$250C(Ru/Rs)_2$$

in which C is the concentration, in mg per ml, of USP Nifedipine RS in the standard preparation, and Ru and Rs are the peak response obtained from assay preparation and standard preparation, respectively.

The dissolution results for Example 15A (uncoated tablets) and Example 15 (coated) and are provided in Table 16 below.

TABLE 16

| | Percent Dissolved | |
|---|---|---|
| Time (hr) | Ex. 15A | Ex. 15 |
| 4 | 12.76 | 13.53 |
| 8 | 36.89 | 42.99 |
| 12 | 73.06 | 63.27 |
| 16 | 98.07 | 73.69 |
| 20 | 102.07 | 78.95 |
| 24 | 106.33 | 87.88 |

As can be seen from the results provided in Table 16, the release of nifedipine from the coated tablets of Example 15 is substantially slowed as compared to the uncoated tablets of Example 15A and therefore appears to be an acceptable 24 hour formulation. However, the results obtained indicate that acceptable 24 hour release formulations may be obtained with or without the hydrophobic coating.

The examples provided above are not meant to be exclusive. Many other variations of the present invention would be obvious to those skilled in the art, and are contemplated to be within the scope of the appended claims.

What is claimed is:

1. A sustained release excipient, comprising:
a gelling agent comprising a heteropolysaccharide gum and a homopolysaccharide gum which crosslinks with said heteropolysaccharide gum when exposed to a fluid in an environment of use, the ratio of said heteropolysaccharide gum to said homopolysaccharide gum being from about 1:3 to about 3:1;

an inert pharmaceutical diluent selected from the group consisting of a monosaccharide, a disaccharide, a polyhydric alcohol, and mixtures thereof, the ratio of said inert diluent to said gelling agent being from about 1:8 to about 8:1; and a pharmaceutically acceptable cationic cross-linking agent capable of crosslinking with said gelling agent when exposed to an environmental fluid.

2. The sustained release excipient of claim 1, wherein said heteropolysaccharide gum comprises xanthan gum and said homopolysaccharide gum comprises locust bean gum.

3. The sustained release excipient of claim 1, wherein said cationic crosslinking agent comprises from about 1 to about 20 percent of said sustained release excipient, by weight.

4. The sustained release excipient of claim 1, wherein said gelling agent, said inert diluent, and said cationic cross-linking agent are granulated with a hydrophobic material selected from the group consisting of an alkylcellulose, a copolymer of acrylic and methacrylic acid esters, waxes, shellac, zein, hydrogenated vegetable oils, and mixtures of any of the foregoing, said hydrophobic material being included in an amount effective to slow the hydration of said gelling agent when exposed to an environmental fluid.

5. The sustained release excipient of claim 4, wherein said hydrophobic material is ethylcellulose.

6. A sustained release excipient comprising:

a sustained release excipient comprising from about 10 to about 99 percent by weight gelling agent, from about 0 to about 89 percent by weight of an inert pharmaceutically acceptable diluent selected from the group consisting of a monosaccharide, a di-saccharide, a polyhydric alcohol, and mixtures thereof, and from about 1 to about 20 by weight of a pharmaceutically acceptable cationic crosslinking agent capable of cross-linking with said gelling agent when exposed to an environmental fluid to increase the gel strength.

7. The sustained release excipient of claim 6, which comprises from about 10 to about 75 percent gelling agent, from about 2 to about 15 percent cationic crosslinking agent, and from about 30 to about 75 percent inert diluent.

8. The sustained release excipient of claim 6, which comprises from about 30 to about 75 percent gelling agent, from about 5 to about 10 percent cationic crosslinking agent, and from about 15 to about 65 percent inert diluent.

9. The sustained release excipient of claim 6, wherein said gelling agent comprises a heteropolysaccharide gum and a homopolysaccharide gum which crosslinks with said heteropolysaccharide gum when exposed to an environmental fluid, the ratio of said heteropolysaccharide gum to said homopolysaccharide gum being from about 3:1 to about 1:3.

10. The sustained release excipient of claim 9, wherein said heteropolysaccharide gum is xanthan gum and said homopolysaccharide gum is locust bean gum.

11. A sustained release excipient, comprising:

a gelling agent;

an inert pharmaceutical diluent selected from the group consisting of monosaccharide, a disaccharide, a polyhydric alcohol, and mixtures thereof, the ratio of said inert diluent to said gelling agent being from about 1:8 to about 8:1;

said gelling agent and said inert pharmaceutical diluent being granulated with a hydrophobic material selected from the group consisting of an alkylcellulose, a hydrophobic cellulosic material, a copolymer of acrylic and methacrylic acid esters, shellac, waxes, zein and mixtures of any of the foregoing, prior to the incorporation of said medicament, said hydrophobic polymer being included in an amount effective to slow the hydration of said gelling agent when exposed to an environmental fluid.

12. The sustained release excipient of claim 11, wherein said gelling agent comprises xanthan gum and locust bean gum in a ratio from about 1:3 to about 3:1.

13. The sustained release excipient of claim 11, wherein said hydrophobic polymer is included in an amount from about 1 to about 20 percent, by weight.

14. The sustained release excipient of claim 11, wherein said hydrophobic polymer is included in an amount form about 1 to about 10 percent, by weight.

15. The sustained release excipient of claim 1 wherein said cationic crosslinking agent is selected from the group consisting of an alkali metal sulfate, an alkali metal chloride, an alkali metal borate, an alkali metal bromide, an alkali metal citrate, an alkali metal acetate, an alkali metal lactate, an alkaline earth metal sulfate, an alkaline earth metal chloride, an alkaline earth metal borate, an alkaline earth metal bromide, an alkaline earth metal citrate, an alkaline earth metal acetate, an alkaline earth metal lactate, and mixtures thereof.

16. The sustained release excipient of claim 1 wherein said cationic crosslinking agent comprises calcium sulfate.

17. The sustained release excipient of claim 6 wherein said cationic crosslinking agent is selected from the group consisting of an alkali metal sulfate, an alkali metal chloride, an alkali metal borate, an alkali metal bromide, an alkali metal citrate, an alkali metal acetate, an alkali metal lactate, an alkaline earth metal sulfate, an alkaline earth metal chloride, an alkaline earth metal borate, an alkaline earth metal bromide, an alkaline earth metal citrate, an alkaline earth metal acetate, an alkaline earth metal lactate, and mixtures thereof.

18. The sustained release excipient of claim 6 wherein said cationic crosslinking agent comprises calcium sulfate.

* * * * *